United States Patent [19]

Bach

[11] Patent Number: 4,765,330

[45] Date of Patent: Aug. 23, 1988

[54] METHOD AND APPARATUS FOR REMOVAL OF PLAQUE FROM BLOOD VESSELS

[76] Inventor: Bert Bach, 370 West End Ave., New York, N.Y. 10023

[21] Appl. No.: 523,262

[22] Filed: Aug. 15, 1983

[51] Int. Cl.⁴ .............................................. A61B 17/36
[52] U.S. Cl. .................................................. 128/303.1
[58] Field of Search ........................................ 128/4–8, 128/303.1

[56] References Cited

U.S. PATENT DOCUMENTS

| | | | |
|---|---|---|---|
| 2,424,064 | 7/1947 | Stegeman | 128/6 |
| 3,131,690 | 5/1964 | Innis et al. | 128/6 |
| 4,108,211 | 8/1978 | Tanaka | 128/4 |
| 4,207,874 | 6/1980 | Choy | 128/6 |
| 4,279,245 | 7/1981 | Takagi et al. | 128/4 |
| 4,313,093 | 1/1982 | Suenaga et al. | 128/303.1 |
| 4,329,980 | 5/1982 | Terade | 128/4 |
| 4,421,382 | 12/1983 | Doi et al. | 128/303.1 |

Primary Examiner—Max Hindenburg
Attorney, Agent, or Firm—Eliot S. Gerber

[57] ABSTRACT

Plaque accumulation in the blood vessels of a patient is removed by a laser beam acting directly on the plaque. The laser beam is conducted to the plaque by a hollow tubular catheter which is sufficiently resilient and flexible so that it may be snaked through a blood vessel to the location of the plaque. The tube has an internal mirrored surface and its internal wall is formed from plastic resin tape having one surface coated with a mirror material. The tape is covered by an elongated spring which, in turn, is covered by a smooth plastic resin coating forming the exterior wall of the tube. In one embodiment the spring is replaced by a series of rings, with each ring having opposed loops to guide wires, with the wires being strung parallel with the axis of the tube. The wires are fastened to the innermost and outermost rings so that manipulation of the outermost ring will selectively pull the wires to direct the direction of the tube.

14 Claims, 4 Drawing Sheets

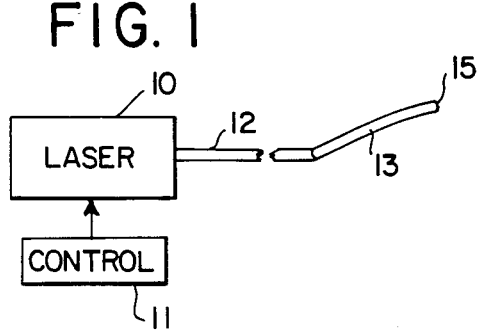
FIG. 1
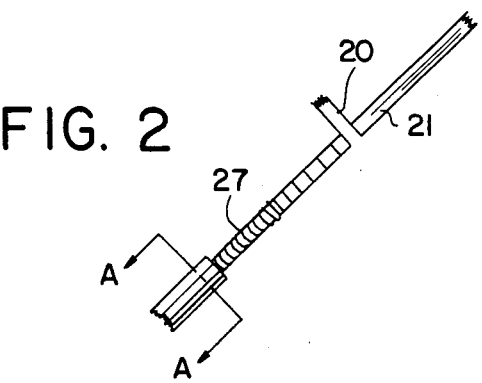
FIG. 2
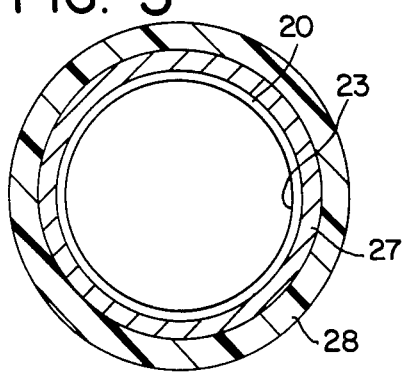
FIG. 3
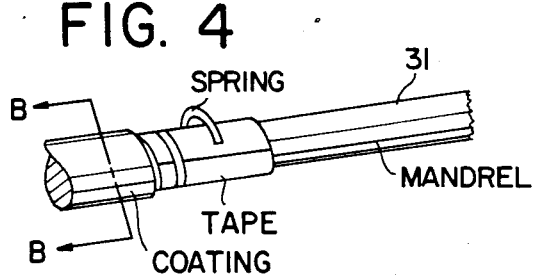
FIG. 4
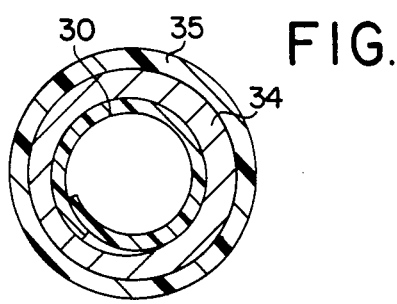
FIG. 5
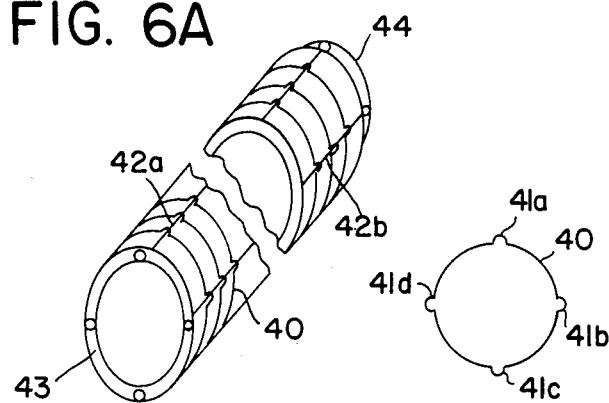
FIG. 6A
FIG. 6B

METHOD AND APPARATUS FOR REMOVAL OF PLAQUE FROM BLOOD VESSELS

BACKGROUND OF THE INVENTION

At the present time it is known that the accumulation of plaque in blood vessels may, under certain circumstances, present a health hazard to patients. For example, the accumulation of plaque may result in lowering the blood pressure to peripheral regions of the body. Additionally, accumulation of plaque in blood vessels associated with the heart may result in increased strain on the heart muscles and may eventually lead to heart failure either due to such strain or to further closure of the blood vessel by the plaque.

It is possible, in many cases, to remove the plaque by an operation in which the blood vessel in which the plaque is accumulated is partially removed by the surgeon. Such operations, particularly when the blood vessels are associated with the heart, may be both costly and present a health risk, especially if the patient is elderly or otherwise in ill health.

OBJECTIVES AND FEATURES OF THE INVENTION

It is an objective of the present invention to provide a device and method for the removal of plaque accumulation in blood vessels without the necessity of operating on the patient by removal of the blood vessel.

It is a further objective of the present invention that the method and device present relatively less of a hazard to the health of the patient as compared with present operating procedures.

It is a further objective of the present invention that the method and device may be used a repeated number of times without presenting an additional health hazard to the patient.

It is a feature of the present invention to provide a device and method for dissolving the plaque which may accumulate in the blood vessels of the patient. The plaque is removed by means of heat which is produced from a high-energy laser source, preferably a gas laser operating in the 20-50 watt range. The heat energy from the laser beam is conducted to the plaque by means of a flexible elongated tube. The internal surface of the tube is highly reflective and is preferably a mirror surface of deposited aluminum or silver. The reflective surface is formed as an internal surface of a flexible plastic resin tube. The tube is prevented from kinking by an elongated helical spring wound about its external surface. Preferably the spring, in turn, is covered by a coating of a suitable plastic resin. In one embodiment the internal mirror surface is formed by winding an elongated flat ribbon (tape) about a mandrel with the inside surface of the tape being the mirror surface. The tape is a flexible plastic resin film. An elongated helical spring is wound about the tape and covered by a liquid plastic resin which, after it dries, forms a unified tubular structure.

In another embodiment the mirror surface is formed by a tape which is overlapped with its overlapping edges being parallel to the axis of the tube. As in the prior embodiment, the mirrored material is covered with a spring which, in turn, is covered with a suitable plastic resin.

The elongated tube is inserted through a vein or artery during the operative procedure until it reaches the plaque accumulation. The plaque accumulation may be seen, using X-ray technology, as it is absorbent to dye. When the tube, which is also easily seen in an X-ray, is positioned next to the plaque, the gas laser is fired. The heat from the gas laser is conducted along the length of the tube and reacts with the plaque, causing its disintegration.

BRIEF DESCRIPTION OF THE DRAWINGS

Other objectives and features of the present invention will be apparent from the following detailed description, taken in conjunction with the accompanying drawings.

In the drawings:

FIG. 1 is a block schematic diagram illustrating the system of the present invention;

FIG. 2 is a perspective view illustrating the construction of the first embodiment of the present invention, in which a tape is wound about a mandrel;

FIG. 3 is a cross-sectional view taken along the line A—A of FIG. 2 and is enlarged to show the various layers of the tube after construction;

FIG. 4 is a perspective view showing the second embodiment of the present invention;

FIG. 5 is an enlarged cross-sectional view taken along the lines B—B of FIG. 3; and FIG. 6 is a perspective view, and FIG. 6B is a front view, illustrating the third embodiment of the present invention, without its outer covering.

DETAILED DESCRIPTION OF THE INVENTION

As shown in FIG. 1, the present invention seeks to disintegrate plaque, which has accumulated in a blood vessel, using heat. The heat is supplied from a suitable laser 10 (light amplification by stimulated emission of radiation). Preferably the laser 10 is a gas laser whose output is in the range of 20-50 watts of power. A suitable laser device would operate in the infrared radiation band ($10^{14}$ to $10^{12}$ Hz). The laser 10 is provided with a suitable control 11 so that its on-off time may be accurately controlled by the surgeon during the operation. The laser 10 produces a coherent beam of light which is conducted by the tube 12 to the tube 13. The tube 12 and 13 may be of the same material, size and construction, the only difference being that the tube 13 is sterile as it is intended to be used in blood vessels of the patient.

During the operation the tube 13 is inserted through the blood vessel of the patient, for example, through the femoral vein and iliac vein, to the point of accumulation of the plaque which may be visualized by means of X-ray. When the end 15 of the tube 13 has reached the plaque, the laser is turned on until the plaque is disintegrated.

The tube 13 to which the present invention is particularly directed is a hollow tubular member having an internal light reflective surface, and is preferably round, in cross-section, in external and internal diameters. The light reflective surface is preferably formed by vacuum deposition (vacuum sputter) of a suitable material, preferably aluminum or silver, on a plastic resin film which is preferably in the form of a tape. The tape may be polytetrafluoroethylene (Teflon, TM of DuPont) or polyethylene. The tape, one side of which after such vacuum deposition has a mirror-like surface, is used to form the tube 13.

In the embodiment illustrated in FIGS. 2 and 3, the tape 20 is wound about a mandrel 21 in an overlapping helix. The tape is arranged so that its internal mirror surface 23 is against the outer surface of the mandrel. The tape forms a complete internal surface for the final tube 13. Although there is a slight loss of conductive light to the edges of the tab, such loss is relatively insignificant because of the short length between the laser and the plaque. The outer surface of the tape 26 is covered by an elongated helical spring 27. The spring may be either a metal spring made of metal which is compatible with the body, or of a plastic spring material. The spring 27 is covered by a coating 28 of a plastic resin which is compatible with the body, for example, polytetrafluoroethylene (TM of DuPont) or polyester plastic from xylene (Mylar, TM of Dow). The outer covering may be formed by heat extrusion over the coil or by other coating techniques. It is not necessary that the plastic be heatable to the extent necessary for sterilization as it is intended that the tube 13 is sufficiently inexpensive so that it could be disposed of after each operation rather than re-used.

In another embodiment, shown in FIGS. 4 and 5, the tape 30, which is the same type of tape as in the prior embodiment, is formed about a mandrel 31 in an extrusion. In this case, however, the tape is folded over itself so that its folded-over internal edge 32 is parallel with imaginary axis 33 of the tube. As in the prior embodiment the external surface of the tape is covered by an elongated helical spring 34. The spring, in turn, is covered by a plastic resin material 35 which is compatible with the body.

In both embodiments the internal surface of the tube is highly reflective at the frequency of the laser. It has been estimated that the loss along the tube may be only 10 or 40%, even though the tube is completely bent in a "U" and may extend for 3 or 4 feet. The tube is flexible so that it may be bent and follow the curves of the patient's blood vessels. At the same time it is sufficiently stiff so that the surgeon may insert it and it will, like other types of surgical catheters, follow the blood vessel.

Variations may be made in the present invention within the scope of the subjoined claims. For example, the laser device may be positioned directly at the entrance of the tube 13 rather than having its laser beam conducted to the tube 13 by the prior tube 12.

The mandrel in all embodiments is removed after the tube is formed. For example it may, if coated with a lubricant, be pulled from within the tube. Alternatively, it may be formed of a material which may be dissolved by a liquid solvent or it may be of a low-heat material, such as wax, and may be removed by heating.

Another variation is that the elongated helical spring may be replaced by a tandem series of rings. The rings, like the spring, prevents kinking of the tube. The rings are preferably evenly spaced along the outer wall of the tape and covered by a plastic resin having a smooth outer wall. When the tube is straight, i.e., its axis is a straight line, the plane of each ring is perpendicular to the axis.

As shown in FIGS. 6A and 6B the rings 40 may be formed with loops 41a–41d. The loops are on opposite sides of the ring, i.e., they are spaced 90° apart and extend outwardly from the center of the ring. A plurality of wires 42a–42d, for example, 3 to 8, in the illustrated case four wires, are strung along the tube (only wires 41a, 41b are shown in FIG. 6A). The wires 42a–42d are used to control the direction of movement of the head (internal orifice) of the tube. The wires 42a–42d are fastened to the outermost ring 43, which may be enlarged for easier manipulation, and to the innermost ring 44 at the inner orifice of the tube. When the operator cants ring 43 (cants it relative to the axis) it pulls one or two of the wires and cants the innermost ring 44 in the same direction as the cant of the outermost ring 43. The canting of the innermost ring 44 acts to curve the tube so that it is guided by the operator through the body vessel, for example, through a vein. The wires are guided by, and are not fastened to, the loops 41a–41d. Each wire may be encased within a plastic tube within which it is freely slidable. The wires are covered by a plastic resin covering having a smooth outer wall, but the covering does not bind the wires, but rather permits their movement. Alternatively, instead of individual rings, a helical spring having loops may be used around the tape.

What is claimed is:

1. A surgical system for the application of heat within a patient's body, including a laser source of coherent heat which source is a gas laser operating in the infrared region and a conduction means connected to said laser source to conduct the laser heat, characterized in that the the conduction means is an elongated hollow and empty flexible bendable and resilient tube adapted to be inserted as a catheter into a body vessel and having an internal wall having a continuous and unbroken mirror surface which remains continuous and unbroken when the tube is bent to conduct the laser heat to a selected internal area of the body.

2. A system as in claim 1 wherein said tube is comprised of an elongated tube having a mirror surface and wound in a helix about the imaginary central longitudinal axis of the tube and the tube also includes a helical spring positioned about the outer surface of the tape to prevent kinking of the tube, and a plastic resin layer covering the spring to provide a smooth outer wall for the tube.

3. A system as in claim 1 wherein said tube is composed of an elongated tape having a mirror surface and overlapped so that its overlapped edge is parallel to the imaginary central longitudinal axis of the tube, and the tube also includes a helical spring positioned about the outer surface of the tape to prevent kinking of the tube, and a plastic resin layer covering the spring to provide a smooth outer wall for the tube.

4. A system as in claim 1 wherein a series of rings are positioned closely together in tandem along the exterior wall of said tube to prevent kinking of the tube and a plastic resin layer covers the rings to provide a smooth outer wall for the tube.

5. A system as in claim 1 wherein the tube includes a tape having a mirror surface forming the internal wall of the tube, a close together tandem series of ring means about the exterior wall of the tape to prevent kinking of the tube, a plurality of wires freely running along the tube outside of the tape and parallel to the axis of the tube, control means at the entrance and exit of the tube fastened to said wires, and a plastic resin outer sleeve about the wires and ring means to provide a smooth outer wall for the tube.

6. A system as in claim 5 wherein the ring means is an elongated helical spring having a plurality of guide means to guide the wires.

7. A system as in claim 5 wherein the ring means is a series of individual rings arranged with their planes normally perpendicular to the axis of the tube, when the tube is not bent, and wherein the rings have a plurality of means to guide the wires.

8. A system as in claim 1 or 6 wherein the guide means are loops which protrude outwardly from the imaginary central longitudinal axis of the tube and which guide but do not restrain the wires.

9. The method of removing plaque from a blood vessel of a patient by progressing an elongated flexible tube along and within the blood vessel until the position of the plaque within the vessel and apply an infrared region laser beam through the tube to the plaque to destroy the plaque, characterized in that the said tube is a hollow and empty tube having a continuous and unbroken mirrored internal surface along its length when curved to reflect said laser light although the same tube may be curved along its length as it is progressed within the blood vessel.

10. The method as in claim 9 wherein the tube is composed of a tape having a mirror surface, a closely spaced tandem series of rings about the tape to prevent kinking, and a plastic resin outer covering.

11. The method as in claim 9 wherein the tube is manipulated as to its direction of travel by pulling on wires freely running along the tube and connected to the internal orifice of the tube.

12. A system for the application of heat, including a gas laser source of coherent heat in the infrared region and a conduction means of conduct the leaser heat, characterized in that, the conduction means is an elongated hollow and empty flexible bendable and resilient tube adapted to be inserted into an elongated tubular member and to be bent and having an internal wall having a continuous and unbroken mirror surface which remains continuous and unbroken when the tube is bent.

13. A system as in claim 12 wherein said tube is comprised of an elongated tube having a mirror surface and wound in a helix about the imaginary central longitudinal axis of the tube, and the tube also includes a helical spring positioned about the outer surface of the tape to prevent kinking of the tube, and a plastic resin layer covering the spring to provide a smooth outer wall for the tube.

14. A system as in claim 12 wherein said tube is composed of an elongated tape having a mirror surface and overlapped so that its overlapped edge is parallel to the imaginary central longitudinal axis of the tube and the tube also includes a helical spring positioned about the outer surface of the tape to prevent kinking of the tube, and a plastic resin layer covering the spring to provide a smooth outer wall for the tube.

* * * * *